(12) United States Patent
Bayer et al.

(10) Patent No.: US 8,574,616 B2
(45) Date of Patent: Nov. 5, 2013

(54) IMPLANT AND METHOD FOR MANUFACTURING SAME

(75) Inventors: Ullrich Bayer, Admannshagen-Bargeshagen (DE); Claus Harder, Uttenreuth (DE); Elisabeta Burean, Erlangen (DE)

(73) Assignee: BIOTRONIK VI Patent AG, Baar (CH)

( * ) Notice: Subject to any disclaimer, the term of this patent is extended or adjusted under 35 U.S.C. 154(b) by 208 days.

(21) Appl. No.: 12/792,510

(22) Filed: Jun. 2, 2010

(65) Prior Publication Data

US 2011/0009952 A1 Jan. 13, 2011

Related U.S. Application Data

(60) Provisional application No. 61/223,414, filed on Jul. 7, 2009.

(51) Int. Cl.
*A61F 2/00* (2006.01)
*A61F 2/06* (2013.01)
*A61L 33/00* (2006.01)

(52) U.S. Cl.
USPC .................... 424/423; 623/1.39; 427/2.24

(58) Field of Classification Search
None
See application file for complete search history.

(56) References Cited

U.S. PATENT DOCUMENTS

| | | | | |
|---|---|---|---|---|
| 5,536,241 A | * | 7/1996 | Zapol | 604/23 |
| 5,759,192 A | * | 6/1998 | Saunders | 606/194 |
| 5,769,884 A | * | 6/1998 | Solovay | 623/1.13 |
| 6,547,888 B1 | * | 4/2003 | Williams et al. | 148/206 |
| 2005/0048193 A1 | * | 3/2005 | Li et al. | 427/2.24 |
| 2008/0188925 A1 | * | 8/2008 | Zhao | 623/1.42 |
| 2009/0192592 A1 | * | 7/2009 | Asgari | 623/1.39 |
| 2010/0112095 A1 | * | 5/2010 | Morris et al. | 424/718 |

* cited by examiner

*Primary Examiner* — Daniel Sullivan
*Assistant Examiner* — Melissa Javier
(74) *Attorney, Agent, or Firm* — Biotech Beach Law Group PC

(57) ABSTRACT

The present invention relates to a method for manufacturing an implant, in particular an intraluminal endoprosthesis, having a body containing metallic material, preferably iron. The following manufacturing method is provided for promotion of the anti-inflammatory effect of the implant: (i) providing the body of the implant; (ii) producing an at least partially closed pore structure in a portion of the structure of the implant body close to the surface; and (iii) incorporating $NO_X$ into the cavities of the pore structure. Also described is an implant manufactured in this manner.

13 Claims, 1 Drawing Sheet

IMPLANT AND METHOD FOR MANUFACTURING SAME

CROSS REFERENCE TO RELATED APPLICATIONS

This invention claims benefit of priority to U.S. provisional patent application Ser. No. U.S. 61/223,414, filed on Jul. 7, 2009; the contents of which is herein incorporated by reference in its entirety.

FIELD OF THE INVENTION

The present invention relates to a method for manufacturing an implant, in particular an intraluminal endoprosthesis.

BACKGROUND OF THE INVENTION

A great variety of medical endoprosthesis or implants for various uses are known from the prior art. Endovascular prostheses or other endoprosthesis, for example stents, fastening elements for bones, for example screws, plates, or nails, surgical suture material, intestinal clamps, vascular clips, prostheses in the region of the cardiac and soft tissue, and anchor elements for electrodes, in particular for pacemakers or defibrillators, are understood to be implants within the meaning of the present invention.

Stents which are used for treatment of stenoses (vascular constrictions) are utilized particularly frequently as implants. Stents have a body in the form of an (optionally open-worked) tubular or hollow cylindrical basic mesh which is open at both longitudinal ends. The tubular basic mesh of such an endoprosthesis is inserted into the blood vessel to be treated and is used to support the vessel. Such stents have become established in particular for the treatment of vascular diseases. Use of stents allows constricted regions in the blood vessels to be expanded, resulting in lumen gain. Although the optimal vessel cross section primarily necessary for successful treatment may be achieved by the use of stents or other implants, the permanent presence of such a foreign body initiates a cascade of microbiological processes which may promote inflammation of the treated blood vessel or a necrotic alteration of the vessel, for example, and which may lead to gradual overgrowth of the stent as the result of plaque formation. In the worst case this alteration of the blood vessel may result in vascular occlusion.

Implants made of a biodegradable material are frequently used at the present time. Such implants have proven to be advantageous with regard to the problems described above.

Suitable materials for the body of biodegradable implants may contain polymers or metals, for example. The body may be composed of several of these materials. The common feature of these materials is their biodegradability. Examples of suitable polymeric compounds include polymers from the group including cellulose, collagen, albumin, casein, polysaccharides (PSAC), polylactide (PLA), poly-L-lactide (PLLA), polyglycol (PGA), poly-D,L-lactide-co-glycolide (PDLLA-PGA), polyhydroxybutyric acid (PHB), polyhydroxyvaleric acid (PHV), polyalkyl carbonates, polyortho esters, polyethylene terephtalate (PET), polymalonic acid (PML), polyanhydrides, polyphosphazenes, polyamino acids, and the copolymers thereof, as well as hyaluronic acid. Depending on the desired characteristics, the polymers may be present in pure form, derivatized form, in the form of blends, or as copolymers. Metallic biodegradable materials are primarily based on alloys of magnesium and iron. The present invention preferably relates to implants whose biodegradable material at least partially contains a metal, preferably iron, manganese, and/or tungsten, in particular an iron-based alloy (referred to below as "iron alloy" for short).

Other metallic materials may also be used as implant materials. Implants containing an iron alloy, in particular iron-containing stents, are particularly economical and easy to manufacture.

The term "biodegradation" refers to chemical, in particular hydrolytic, enzymatic, and other metabolic degradation processes in the living organism, which are primarily caused by the bodily fluids which come into contact with the biodegradable material of the implant, resulting in gradual dissolution of the structures of the implant containing the biodegradable material. As a result of this process the implant loses its mechanical integrity at a specific time. The term "biocorrosion" is often used synonymously for "biodegradation." The term "bioabsorption" includes the subsequent absorption of the degradation products by the living organism.

In the future, it would be desirable to avoid or reduce to the greatest extent possible the above-described inflammation-promoting effect of implants, since this decreases the effectiveness of the implant and may cause further damage to the organism being treated.

U.S. Pat. No. 6,613,432 B2 discloses a plasma treatment in a plasma comprising nitrogen-containing and oxygen-containing molecules for reduction of the inflammatory reaction and for avoidance of restenosis. The plasma treatment is very brief, lasting less than approximately five minutes, for example. However, such a plasma treatment of implants requires complicated equipment and involves a high level of manual effort. Filigreed components such as stents require intricate fine motor skills for the charging procedures which currently are not achievable using automatic handling systems. Furthermore, such plasma treatments result in loading with materials having anti-inflammatory activity only directly at the surface, i.e., to a depth of a few nm. When the subsequent degradation process reaches zones farther in the interior which are not reached by the plasma treatment, there is no longer any anti-inflammatory activity. During the degradation, these interior zones are sometimes already reached very soon after the implant is inserted into the bodily part to be treated, after the time at which further inflammatory reactions are to be suppressed. In addition, it must be assumed that only relatively small quantities of active substances which reduce inflammation can be delivered from a plasma coating to the vessel wall.

SUMMARY OF THE INVENTION

A feature of the present invention, therefore, is to provide a simple and economical method for manufacturing an implant, preferably made of a metallic material, which promotes a prolonged anti-inflammatory effect of the implant after introduction into the organism being treated. It is an aim that no solid or liquid materials are released. A further aim is to minimize interaction with the material of the implant body or the reaction products thereof. Accordingly, a further object of the invention is to provide such an implant.

The feature stated above is achieved by a method comprising the following steps: (i) providing the body of the implant; (ii) producing an at least partially closed pore structure in a portion of the structure of the implant body close to the surface; and (iii) incorporating $NO_X$ into the cavities of the pore structure.

In the present invention the body of the implant includes at least a portion of the implant, preferably the major portion of the implant, which imparts mechanical integrity to the implant.

In method step (ii), the method according to the invention produces a pore structure close to the surface which contains pores (also referred to below as spaces, microcaverns, or voids). This pore structure contains at least partially closed pores. This is followed by incorporation of nitrogen oxides (also referred to as nitrous gases or $NO_X$) into the cavities of the pore structure produced in step (ii) by means of chemisorption, adsorption, or gas filling. During the period of residence of the implant in the treated organism, in particular for degradation of the regions of the implant close to the surface, these compounds are released and exert positive biological effects on the surrounding cell tissue. As the result of its radical interceptor properties $NO_X$ has a particular anti-inflammatory effect as well as antibacterial and cytostatic effects. A constant release of even small doses of $NO_X$ over a long period of time is extremely desirable, particularly in the vascular region.

$NO_X$ is preferably incorporated into the spaces created by the previous expulsion of $CO_X$ compounds in the structure close to the surface. Accordingly, the pores thus produced are not to be construed as macroscopic pores, but instead represent microscopic structures with a diameter of less than 1 μm. Since the molecular radius of the $NO_X$ compounds is smaller than that of the $CO_X$ compounds, the reoccupation of these spaces is favored from a crystallographic standpoint. Particularly high loading with $NO_X$ is achieved when the loading is carried out directly after annealing. Otherwise, the spaces immediately recombine with the remainder of the structure. This impairs the diffusion of $NO_X$ and results in a lower absolute loading of $NO_X$.

The spaces themselves are located primarily in the vicinity of the grain boundaries, since on the one hand the grain boundary diffusion for $NO_X$ present at this location is greater than the diffusion through the grain interior, but on the other hand the defect density and thus the solvency for foreign compounds is also greater. As a result, the loading with $NO_X$ may preferably be increased by providing predominantly small grains in the structure which have a higher grain boundary density.

The term "structure" below refers to the configuration of components of solids (solid bodies), in particular the configuration of the crystallites (grains), pores, amorphous regions, and grain to boundary regions of the implant body. In addition, the term "structure close to the surface" refers to a volume region of the structure of the implant body which extends from the surface to a specified (low) depth of the implant body. This volume region of the implant body extending from the surface to a specified depth is also referred to as "boundary layer of the implant body close to the surface," or "boundary layer" for short. The term "crystal structure" refers to the configuration of atoms within a crystallite (grain).

A further advantage of the method according to the invention is that the release of $NO_X$ is not associated with release of a solid or liquid material. Furthermore, no interactions of the $NO_X$ gas with the material of the implant or reaction products of this material during degradation have been observed thus far.

It is also advantageous that a large quantity of gaseous $NO_X$ can be bound due to the large surface present in the pores or microcaverns.

In one preferred exemplary embodiment, the pore structure is produced by heat treatment of the implant body in an oxygen- and/or carbon-containing atmosphere, and/or by heat treatment under vacuum. Heat treatment is a particularly simple and economical process which provides the necessary conditions for incorporating a $NO_X$ gas.

It is also advantageous that the pore structure of the implant body can act as a material reservoir for a further coating, described in greater detail below, using a pharmaceutically active substance, which is incorporated in the form of nano- or microparticles and which may include, for example, bone growth-promoting substances such as calcium phosphate, contrasting agents which act on a short-term basis, and/or cell growth-inhibiting radioactive substances. In addition, lubricants for reducing the coefficient of friction in a catheter may be effectively incorporated into the pore structure.

Particularly effective incorporation of $NO_X$ gas into the pore structure is achieved by incorporating NO gas into the structure and/or the crystal structure by applying a gauge pressure of at least 5 bar, preferably at least 8 bar. Pure NO gas or a mixture of NO gas with other gases may be used.

It is also advantageous after step (iii) to coat the implant body, at least on a portion of its treated surface, with a polymer, preferably a polymer from the group including magnesium stearate, parylene, and pharmaceutically active substances.

Within the meaning of the invention, a "pharmaceutically active substance" (or therapeutically active substance, active ingredient) is understood to mean a plant, animal, or synthetic active substance (medicament) or a hormone which in appropriate dosages is used as a therapeutic agent for influencing states or functions of the body, as a substitute for active substances such as insulin which are naturally produced by the human or animal body, and for eliminating or rendering harmless pathogenic agents, tumors, cancer cells, or substances foreign to the body. The release of the substance into the environment of the implant has a positive effect on the healing process, or counteracts pathological changes in the tissue resulting from surgical procedures, or in the field of oncology is used to render malignant cells harmless.

These types of pharmaceutically active substances have an anti-inflammatory and/or antiproliferative and/or spasmolytic effect, for example, (optionally in addition to the $NO_X$ that is present), by means of which restenosis, inflammation, or (vascular) spasms, for example, may be avoided. Such substances may be composed, for example, of one or more substances from the active substance group of calcium channel blockers, lipid regulators (fibrates, for example), immunosuppressants, calcineurin inhibitors (tacrolimus, for example), antiphlogistic agents (cortisone or dichlofenac, for example), anti-inflammatory agents (imidazole, for example), antiallergic agents, oligonucleotides (dODN, for example), estrogens (genistein, for example), endothelium-forming agents (fibrin, for example), steroids, proteins, hormones, insulins, cytostatic agents, peptides, vasodilators (sartane, for example), and substances with antiproliferative activity, taxole or taxane, in the present case preferably paclitaxel or sirolimus, everolimus, biolimus A9, deforolimus, and derivatives or prodrugs thereof.

A coating of the boundary layer of the implant close to the surface provided with $NO_X$, using parylene and/or magnesium stearate, is advantageous because the surface characteristics present during production, before the application of parylene and/or magnesium stearate, are acquired, i.e., literally "frozen," as a result of the overlying coating. In this manner it is possible to adjust the surface characteristics, which otherwise may depend on the duration of storage or transport of the implant until it is introduced into the organism to be treated, and thus also the duration of degradation, in a reproducible and defined manner. In addition, the release of $NO_X$ may be controlled. This effect is based on the action as a diffusion barrier with respect to the permeation of water molecules and chloride ions.

For coating with parylene the high gap clearance of parylene has an advantageous effect, also resulting in deep penetration of the pore structure produced by the heat treatment. For parylene, in particular parylene N, the characteristic permeation properties for water, chloride-containing solutions, and hydrogen in conjunction with the underlying surface provide a particularly well-controllable degradation characteristic of the implant. This is also characterized by slow, uniform progression of corrosion over the cross section of the implant. In addition, the parylene layer further assists in avoiding or preventing crack propagation under mechanical load, and prevents partial detachment of the layer.

"Parylene" refers to completely linear, partially crystalline, uncrosslinked aromatic polymers. The various polymers have different properties, and may be divided into four different basic types: parylene C, parylene D, parylene N, and parylene F. Parylene N is preferably used for the further coating after tribochemical treatment.

By use of the method according to the invention, for the coating with magnesium stearate an implant may be manufactured which is characterized by freedom from defects in the body surface as the result of subsequent sealing. Localized spaces and/or pores present on the body surface of the implant are effectively protected from contact with corrosive bodily fluids. The hydrophobic surface characteristic and the low water of crystallization content of the magnesium stearate, which is also achieved by a preferentially performed drying step following application of the magnesium stearate coating, limit the diffusion of water into the base material of the implant body during subsequent storage and transport of the implant. Likewise, particles with low binding tendencies are prevented from detaching from the surface of the implant body during dilation. These particles remain in the tough, highly flexible magnesium stearate layer. This results in increased hemocompatability or biocompatibility.

The magnesium stearate coating of the implant body advantageously reduces the coefficient of friction of the implant. As a result, less force is necessary to push a stent, for example in the form of an implant, within a catheter. In the case of a stent, this allows the stent to be fixed in place more accurately. In addition, crimping and subsequent release of the implant at the site of treatment are simplified.

In one preferred exemplary embodiment of the method according to the invention, the magnesium stearate coating is applied by dipping into a solution, the solution containing magnesium stearate and a solvent, preferably acetone and/or isopropanol, and preferably having a temperature between approximately 10° C. and the particular boiling point of the solvent. Alternatively, the magnesium stearate layer may be applied in such a way that the referenced solution containing magnesium stearate is sprayed onto the body of the implant (spray coating). The part is suspended on a thin wire in a chamber and is sprayed on all sides using a rotating plate (charge holder).

In one preferred exemplary embodiment the effectiveness of the dipping process may be improved by applying a pressure which is less than ambient pressure, preferably less than approximately 90% of ambient pressure, i.e., the atmospheric pressure at the location where the dipping process is carried out. The resulting degassing effect leads to rapid filling of the filigreed surface structure of the implant with magnesium stearate. After a residence time of several minutes in the solution, preferably at least approximately 2 minutes, the implant body coated with magnesium stearate is removed from the dipping bath and dried in a drying oven at a temperature which is higher than room temperature, preferably higher than approximately 30° C. It is particularly preferred for the drying temperature to be as low as possible, i.e., between approximately 40° C. and approximately 70° C., since this results in slow liberation/evaporation of the at least one solvent, thereby producing a pore-free layer containing magnesium stearate.

In one preferred exemplary embodiment the body of the implant preferably contains a degradable metallic material, preferably predominantly iron, in particular greater than 90% by weight iron, particularly preferably at least 99% by weight iron, in particular in an alloy. Alternatively or additionally, manganese and/or tungsten may be used as further metallic materials. Because they may be economically manufactured, these implants are particularly desirable for use in the treatment of diseases of the human or animal organism.

The above-stated object is further achieved by use of an implant which may be obtained by one of the methods according to the invention described above. Such an implant has the advantages referenced above in conjunction with the manufacturing method according to the invention. The morphology of the boundary layer close to the surface as a result of the heat treatment and incorporation of $NO_X$ gas as well as the composition of this boundary layer are characteristic for this treatment, and are identifiable in the manufactured implant.

The above-stated object is further achieved by use of an implant whose body has an at least partially closed pore structure (space structure) in a portion of its structure close to the surface which includes a $NO_X$-containing gas. The advantages described above are also achieved for this implant according to the invention.

In one preferred exemplary embodiment the pores of the pore structure have a maximum diameter of approximately 1 μm.

Furthermore, it is advantageous for the pores of the pore structure to extend to a maximum depth of approximately 15 μm, preferably approximately 10 μm to approximately 15 μm, measured from the surface of the implant body. In one preferred exemplary embodiment the concentration of the $NO_X$ gas in the structure of the implant body close to the surface, which is present in the boundary region close to the surface, is approximately 10% by volume. The depth of approximately 15 μm is achieved for a comparatively practicable process duration of 2 to 4 hours at a treatment pressure of 10 bar in a $NO_X$ atmosphere. This penetration depth and the associated volume of incorporated $NO_X$ (approximately 10% by volume) in the structure are sufficient to achieve anti-inflammatory effects over a period of several days to 4 weeks after introducing the implant at the site of treatment. Only after this period has elapsed is the degradation progressed far enough that component regions which no longer have an elevated concentration of $NO_X$ come into contact with bodily fluid (electrolyte).

Longer treatment times and/or higher process pressures would result in $NO_X$ concentrations which could cause mechanical damage of the structure regions of the treated implant close to the surface. Such damage could result in excessive embrittlement and associated formation of unstable cracks, possibly leading to loss of integrity of the internal structure of the implant.

It is also preferred for the surface of the implant body to have a coating, at least in places, containing a polymer, preferably a polymer from the group including magnesium stearate, parylene, and pharmaceutically active substances. Preferred layer thicknesses of the parylene coating are between approximately 0.5 μm and approximately 2.0 μm. The preferred thickness of the magnesium stearate coating is approximately 0.5 μm to approximately 2.0 μm, preferably approximately 0.7 μm to approximately 1.0 μm. The concentration of magnesium stearate in the coating is approximately between 80% by weight and 100% by weight.

By use of the coating of magnesium stearate and/or parylene the degradation time of the implant may be varied over a broad range, depending on the particular intended use of the implant, and adjusted in a defined manner.

The method according to the invention and the implant according to the invention are explained below with reference to the figures. All of the described and/or illustrated features constitute the subject matter of the invention, regardless of their summary in the claims or back-references.

DESCRIPTION OF THE DRAWINGS

The invention is described based on the attached drawings.

DETAILED DESCRIPTION OF THE INVENTION

Figure 1:
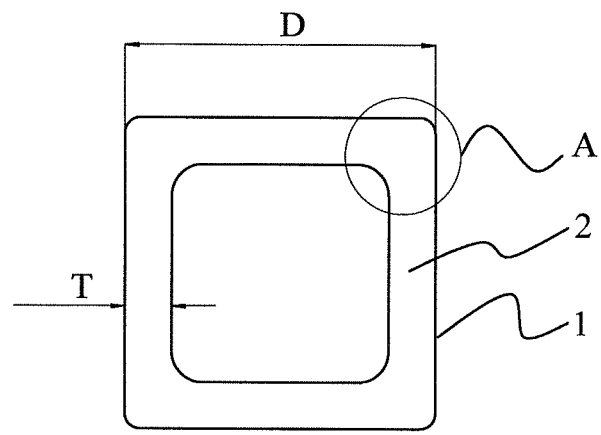
FIG. 1 shows a strut of an implant according to the invention in a cross-sectional view.

FIG. 1 illustrates the cross section of a stent strut 1 according to the invention, which in an outer boundary region 2 close to the surface which originates from the surface of the stent strut and extends to a depth T has an at least partially closed pore structure in which $NO_X$ is incorporated at a concentration of approximately 10% by volume. The dimension T of region 2 containing $NO_X$ is approximately 10 μm to 15 μm. The diameter D of the stent strut 1 is approximately 100 μm.

At this point it is expressly noted that the above-referenced $NO_X$ concentration in the innermost portion of region 2 (indicated by a dashed line) gradually decreases in the direction of the starting composition of the stent strut material, so that the concentration of $NO_X$ changes gradually and does not abruptly decrease at that location. The composition of the stent strut material inside the strut (within the dashed line) essentially corresponds to the starting composition before use of the method according to the invention.

Figure 2:
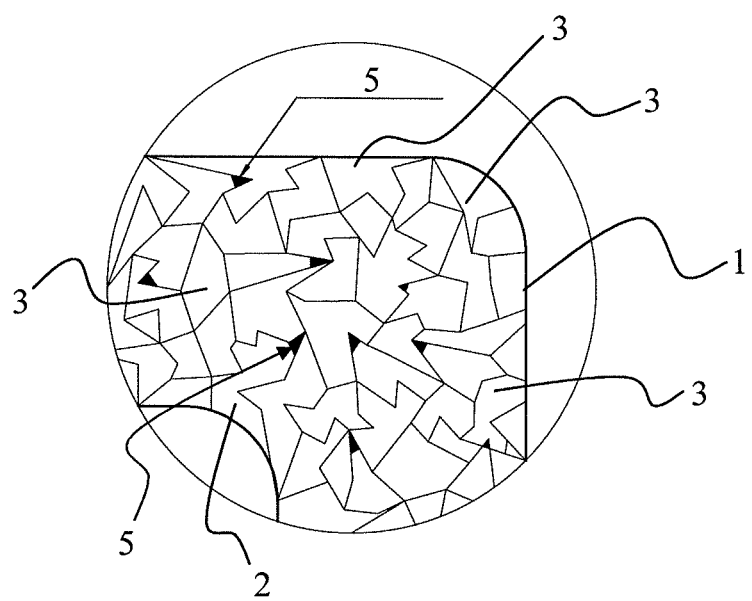
FIG. 2 shows an enlarged section of the exemplary embodiment illustrated in FIG. 1.

FIG. 2 shows an enlarged section of the cross section illustrated in FIG. 1, in region A. In section A of the strut 1 grains 3 are visible in the structure of the stent strut material. $NO_X$ has been incorporated into micropores of the structure in which $CO_X$ compounds were previously present, located in particular in the regions of the grain boundaries marked in black and denoted by reference numeral 5, in particular in the grain boundary interstices. The incorporation of $NO_X$ into the pore structure has been performed according to one of the methods according to the invention described below. $NO_X$ has a particular anti-inflammatory effect during the degradation of the stent according to the invention after the stent is inserted into the blood vessel to be treated.

EXAMPLE 1

A stent having a body composed of an iron-based alloy containing at least 98% by weight iron, for example the alloys C10, C15, or C20, is subjected to reducing heat treatment at a temperature of approximately 850° C. in a carrier gas containing carbon (for example, a mixture of 60% by volume methanol and 40% by volume nitrogen) for approximately 1.5 hours. During this process, generally referred to as gas carburization, gaseous carbon monoxide dissociates into atomic carbon and oxygen at the surface of the part being treated. The carbon atoms are absorbed by the metal and subsequently diffuse into the stent surface. The depth of diffusion and the carbon gradient in the matrix of the iron alloy may be varied, depending on the duration of treatment. The parameters of gas mixture, time, temperature, and concentration of the carbon-containing gas in particular may be varied (as an additional inert gas, argon is able to reduce the available carbon, and thus, the carbon diffusion). The carbon concentration in the structure region close to the surface increases as the available carbon, time, and temperature increase. The carbon also penetrates deeper into the structure. The stent is then annealed in an oxygen-containing, i.e., oxidizing, atmosphere, for example containing 50% by volume nitrogen and 50% by volume oxygen, at a temperature of approximately 800° C. over a period of 1.5 hours. This results in the generation of carbon oxides (primarily $CO_2$ on account of the excess oxygen). These gases escape from the structure of the stent body close to the surface. The surface-decarburized zone thus obtained has a depth T of 10 to 15 μm.

The degassing effect may be accelerated by annealing at approximately 800° C. under vacuum after the oxidizing process. For example, a vacuum of at least $10^{-4}$ Pa is maintained over a period of at least three hours, so that the $CO_X$ compounds contained in the stent body escape from the cavities (pores). The vacuum treatment also causes a reduction in the oxide layer which forms at the surface and acts as a diffusion barrier, thus allowing the $CO_X$ compounds to escape more quickly from the stent surface.

The heat treatment produces a porous structure close to the surface in the stent body which is interspersed with microcaverns (pores). Aeration with NO gas is then performed in the same treatment chamber in which the reduction, oxidation, and vacuum annealing have been carried out. The NO gas is injected into the cavities at a gauge pressure of up to approximately 10 bar. The microcaverns are enriched with $NO_X$ gas as a result of this treatment.

After completion of the $NO_X$ loading the stent is removed from the treatment chamber and installed in a catheter. Subsequent storage of the stent, installed in a catheter, in air or under protective gas at standard pressure results in only slight escape of the $NO_X$ compounds from the stent body.

As described below, the surface of the stent may be subsequently sealed with a degradable or nondegradable polymer.

In the course of treatment with the stent manufactured in this manner, mechanical load, for example during dilation of the stent, causes cracks in the zones of the stent subject to the most severe plastic deformation. These cracks extend into the pores and thus promote the release of the incorporated $NO_X$ gas.

EXAMPLE 2

Analogous to Example 1, with the following composition of the material of the stent (iron-based alloy containing Mn as stent material): Fe alloy containing 82% by weight Fe, 15% by weight Mn, and 3% by weight Pd (Fe82Mn15Pd3). Hydrogen sulfide is used as carrier gas for cavity production.

EXAMPLE 3

For all stents manufactured according to Examples 1 and 2, as the final step a coating of parylene C, magnesium stearate, and/or a pharmaceutically active substance may be applied.

The coating with parylene C is carried out in the gas phase. A layer thickness of approximately 0.5 μm is achieved after approximately one-half hour coating time.

Short-term corrosion protection may be achieved by use of a parylene coating. The surface to condition is "frozen." Thus, there is no uncontrolled automatic degradation before the endoprosthesis is provided at the installation site.

The same objective is pursued with the magnesium stearate coating described below. After carrying out exemplary embodiments 1 through 3 and subsequent drying, the endoprosthesis is suspended on a plastic thread (polyamide, for example) and dipped into the solution for application of the magnesium stearate. The solution consists of nine parts ultrapure acetone or isopropanol and one part magnesium stearate, for example. The dipping process is carried out at room temperature in an evacuatable desiccator. A negative pressure of approximately 100 mbar is generated using a pump. In this manner the filigreed microporous surface structures produced by the previous plasma-chemical pretreatment, i.e., the undercuts and structures with complicated shapes, are effectively freed of residual gas. Full coverage of the stent surface by the magnesium stearate, which also penetrates into the surface structures and undercuts, may thus be performed in the solution. After a residence time of approximately 3 minutes in the dipping bath the desiccator is ventilated, and the implant is removed from the dipping bath and dried in a convection cabinet, still suspended by the plastic thread, at a temperature of 60° C. The layer thickness of the magnesium stearate coating thus obtained is in the range of approximately 0.5 µm to approximately 10 µm.

Due to the negative pressure present in the desiccator the magnesium stearate is deposited very uniformly on the surface. A low drying temperature advantageously causes slow release/evaporation of the solvents in the dipping solution, resulting in a pore-free magnesium stearate layer. If the implant manufactured in this manner is a stent, the body provided with the first layer and intermediate layer may then be finished out with a catheter and subjected to radiation sterilization.

Analogously to the production of the parylene or magnesium stearate coating, the surface of the implant may alternatively or additionally be coated with a pharmaceutically active substance. Preferred substances are stated in the description above.

It will be apparent to those skilled in the art that numerous modifications and variations of the described examples and embodiments are possible in light of the above teaching. The dis-closed examples and embodiments are presented for purposes of illustration only. Therefore, it is the intent to cover all such modifications and alternate embodiments as may come within the true scope of this invention.

What is claimed is:

1. A method for manufacturing a vascular implant, having a body containing metallic material comprising the following steps:
   i) providing the body of the implant;
   ii) producing an at least partially closed pore structure in a portion of the structure of the implant body close to the surface, comprising a reducing step followed by an annealing step in an oxidizing atmosphere, wherein the pore structure comprises microscopic structures having a diameter of less than 1 µm; and
   iii) incorporating $NO_x$ into the cavities of the pore structure.

2. The method according to claim 1, wherein the reducing step comprises heat treatment of the implant body in a carbon-containing atmosphere.

3. The method according to claim 1, wherein the $NO_x$ is incorporated into the pore structure by applying a gauge pressure of at least 5 bar or at least 8 bar.

4. The method according to claim 1, wherein after step iii) the implant body is coated, at least on a portion of its surface, with a polymer.

5. The method according to claim 1, wherein the body of the implant is greater than 90% by weight iron or greater than 99% by weight iron.

6. The method according to claim 1, wherein the pore structure has a maximum depth of 15 µm.

7. The method according to claim 6, wherein the pore structure has a depth between 10 µm to 15 µm.

8. The method according to claim 1, wherein the step of producing at least one partially closed pore structure further comprises a vacuum annealing step after oxidation from the oxidizing atmosphere.

9. The method according to claim 8, wherein the reducing step, annealing step, vacuum annealing step and step of incorporating $NO_x$ is performed in a same treatment chamber.

10. The method according to claim 1, wherein the reducing step, annealing step and step of incorporating $NO_x$ is performed in a same treatment chamber.

11. The method according to claim 1, wherein the vascular implant is an intraluminal endoprosthesis.

12. The method according to claim 1, wherein the implant comprises an iron alloy.

13. The method according claim 4, wherein the polymer is selected from the group consisting of magnesium stearate, parylene, and a pharmaceutically active substance.

* * * * *